(12) United States Patent
Nieminen et al.

(10) Patent No.: US 11,033,257 B2
(45) Date of Patent: *Jun. 15, 2021

(54) TISSUE SHAPING DEVICE

(71) Applicant: Cardiac Dimensions Pty. Ltd., Kirkland, WA (US)

(72) Inventors: Gregory D. Nieminen, Bothell, WA (US); Nathan Aronson, Chico, CA (US)

(73) Assignee: Cardiac Dimensions Pty. Ltd., Kirkland, WA (US)

( * ) Notice: Subject to any disclaimer, the term of this patent is extended or adjusted under 35 U.S.C. 154(b) by 7 days.

This patent is subject to a terminal disclaimer.

(21) Appl. No.: 16/275,920

(22) Filed: Feb. 14, 2019

(65) Prior Publication Data

US 2019/0262136 A1 Aug. 29, 2019

Related U.S. Application Data

(63) Continuation of application No. 15/465,253, filed on Mar. 21, 2017, now Pat. No. 10,206,778, which is a
(Continued)

(51) Int. Cl.
*A61F 2/24* (2006.01)
*A61B 17/00* (2006.01)
(Continued)

(52) U.S. Cl.
CPC ........ *A61B 17/00234* (2013.01); *A61F 2/246* (2013.01); *A61F 2/2442* (2013.01);
(Continued)

(58) Field of Classification Search
CPC ......... A61F 2/24; A61F 2/2448; A61F 2/2445
(Continued)

(56) References Cited

U.S. PATENT DOCUMENTS 3,620,212 A 11/1971 Fannon, Jr. et al.
3,786,806 A 1/1974 Johnson et al.
(Continued)

FOREIGN PATENT DOCUMENTS

EP 0893133 A1 1/1999
EP 0903110 A1 3/1999
(Continued)

OTHER PUBLICATIONS

El-Maasarany et al.; The coronary sinus conduit function: Anatomical study (relationship to adjacent structures); http://europace.oxfordjournals.org/cge/content/full/7/5/475. (accessed Sep. 9, 2008).
(Continued)

*Primary Examiner* — Suzette J Gherbi
(74) *Attorney, Agent, or Firm* — Shay Glenn LLP; Thomas M. Zlogar (57) ABSTRACT

In one embodiment, the present invention relates to a tissue shaping device adapted to be disposed in a vessel near a patient's heart to reshape the patient's heart. Such tissue shaping device can include an expandable proximal anchor; a proximal anchor lock adapted to lock the proximal anchor in an expanded configuration; an expandable distal anchor; a distal anchor lock adapted to lock the distal anchor in an expanded configuration; and a connector disposed between the proximal anchor and the distal anchor, the connector having a substantially non-circular cross-section.

3 Claims, 5 Drawing Sheets

Related U.S. Application Data continuation of application No. 15/136,739, filed on Apr. 22, 2016, now Pat. No. 9,597,186, which is a continuation of application No. 14/642,476, filed on Mar. 9, 2015, now Pat. No. 9,320,600, which is a continuation of application No. 12/907,907, filed on Oct. 19, 2010, now Pat. No. 8,974,525, which is a continuation of application No. 12/060,781, filed on Apr. 1, 2008, now Pat. No. 7,828,842, which is a continuation of application No. 11/275,630, filed on Jan. 19, 2006, now Pat. No. 7,351,260, which is a continuation-in-part of application No. 11/132,786, filed on May 18, 2005, now abandoned.

(60) Provisional application No. 60/645,819, filed on Jan. 20, 2005.

(51) Int. Cl.
    *A61N 1/05* (2006.01)
    *A61B 17/12* (2006.01)

(52) U.S. Cl.
    CPC .......... *A61F 2/2451* (2013.01); *A61F 2/2466* (2013.01); *A61B 2017/00243* (2013.01); *A61B 2017/00867* (2013.01); *A61B 2017/1205* (2013.01); *A61B 2017/12054* (2013.01); *A61F 2/24* (2013.01); *A61F 2/2448* (2013.01); *A61F 2210/0014* (2013.01); *A61F 2220/0008* (2013.01); *A61F 2250/0012* (2013.01); *A61F 2310/00017* (2013.01); *A61F 2310/00023* (2013.01); *A61N 1/057* (2013.01); *A61N 2001/0585* (2013.01)

(58) Field of Classification Search
    USPC ................................. 623/2.36–2.38
    See application file for complete search history.

(56) References Cited

U.S. PATENT DOCUMENTS

| | | |
|---|---|---|
| 3,890,977 A | 6/1975 | Wilson |
| 3,974,526 A | 8/1976 | Dardik et al. |
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,099,838 A | 3/1992 | Bardy |
| 5,104,404 A | 4/1992 | Wolff |
| 5,197,978 A | 3/1993 | Hess |
| 5,250,071 A | 10/1993 | Palermo |
| 5,261,916 A | 11/1993 | Engelson |
| 5,265,601 A | 11/1993 | Mehra |
| 5,344,426 A | 9/1994 | Lau et al. |
| 5,350,420 A | 9/1994 | Cosgrove et al. |
| 5,411,549 A | 5/1995 | Peters |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,617,854 A | 4/1997 | Munsif |
| 5,662,703 A | 9/1997 | Yurek et al. |
| 5,676,671 A | 10/1997 | Inoue |
| 5,733,325 A | 3/1998 | Robinson et al. |
| 5,733,328 A | 3/1998 | Fordenbacher |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,001,118 A | 12/1999 | Daniel et al. |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,045,497 A | 4/2000 | Schweich, Jr. et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,159,220 A | 12/2000 | Gobron et al. |
| 6,162,168 A | 12/2000 | Schweich, Jr. et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,306,141 B1 | 10/2001 | Jervis |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,368,345 B1 | 4/2002 | Dehdashtian et al. |
| 6,395,017 B1 | 5/2002 | Dwyer et al. |
| 6,402,781 B1 | 6/2002 | Langberg et al. |
| 6,409,750 B1 | 6/2002 | Hyodoh et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,478,776 B1 | 11/2002 | Rosenman et al. |
| 6,503,271 B2 | 1/2003 | Duerig et al. |
| 6,537,314 B2 | 3/2003 | Langberg et al. |
| 6,556,873 B1 | 4/2003 | Smits |
| 6,562,066 B1 | 5/2003 | Martin |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |

(56) References Cited

U.S. PATENT DOCUMENTS

| | | | |
|---|---|---|---|
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,798,231 B2 | 9/2004 | Iwasaki et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,827,690 B2 | 12/2004 | Bardy |
| 6,881,220 B2 | 4/2005 | Edwin et al. |
| 6,890,353 B2 | 5/2005 | Cohn et al. |
| 6,899,734 B2 | 5/2005 | Castro et al. |
| 6,908,478 B2 | 6/2005 | Alferness et al. |
| 6,908,482 B2 | 6/2005 | McCarthy et al. |
| 6,926,690 B2 | 8/2005 | Renati |
| 6,935,404 B2 | 8/2005 | Duerig et al. |
| 6,949,122 B2 | 9/2005 | Adams et al. |
| 6,955,689 B2 | 10/2005 | Ryan et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 7,004,958 B2 | 2/2006 | Adams et al. |
| 7,087,064 B1 | 8/2006 | Hyde |
| 7,152,605 B2 | 12/2006 | Khairkhahan et al. |
| 7,175,653 B2 | 2/2007 | Gaber |
| 7,179,282 B2 | 2/2007 | Alferness et al. |
| 7,270,676 B2 | 9/2007 | Alferness et al. |
| 7,276,078 B2 | 10/2007 | Spenser et al. |
| 7,309,354 B2 | 12/2007 | Mathis et al. |
| 7,311,729 B2 | 12/2007 | Mathis et al. |
| 7,316,708 B2 | 1/2008 | Gordon et al. |
| 7,351,260 B2 * | 4/2008 | Nieminen | A61F 2/246 |
| | | | 623/2.36 |
| 7,364,588 B2 | 4/2008 | Mathis et al. |
| 7,452,375 B2 | 11/2008 | Mathis et al. |
| 7,503,931 B2 | 3/2009 | Kowalsky et al. |
| 7,591,826 B2 | 9/2009 | Alferness et al. |
| 7,608,102 B2 | 10/2009 | Adams et al. |
| 7,635,387 B2 | 12/2009 | Reuter et al. |
| 7,674,287 B2 | 3/2010 | Alferness et al. |
| 7,758,639 B2 | 7/2010 | Mathis |
| 7,794,496 B2 * | 9/2010 | Gordon | A61F 2/2451 |
| | | | 623/2.36 |
| 7,814,635 B2 | 10/2010 | Gordon |
| 7,828,841 B2 | 11/2010 | Mathis et al. |
| 7,828,842 B2 * | 11/2010 | Nieminen | A61F 2/2466 |
| | | | 623/2.36 |
| 7,828,843 B2 | 11/2010 | Alferness et al. |
| 7,837,728 B2 * | 11/2010 | Nieminen | A61F 2/2451 |
| | | | 623/2.36 |
| 7,837,729 B2 | 11/2010 | Gordon et al. |
| 7,887,582 B2 | 2/2011 | Mathis et al. |
| 7,955,384 B2 | 6/2011 | Rafiee et al. |
| 8,006,594 B2 | 8/2011 | Hayner et al. |
| 8,062,358 B2 | 11/2011 | Mathis et al. |
| 8,075,608 B2 | 12/2011 | Gordon et al. |
| 8,172,898 B2 | 5/2012 | Alferness et al. |
| 8,182,529 B2 | 5/2012 | Gordon et al. |
| 8,250,960 B2 | 8/2012 | Hayner et al. |
| 8,439,971 B2 | 5/2013 | Reuter et al. |
| 8,974,525 B2 * | 3/2015 | Nieminen | A61F 2/2451 |
| | | | 623/2.36 |
| 9,320,600 B2 * | 4/2016 | Nieminen | A61F 2/246 |
| 9,408,695 B2 | 8/2016 | Mathis et al. |
| 9,474,608 B2 | 10/2016 | Mathis et al. |
| 9,526,616 B2 * | 12/2016 | Nieminen | A61F 2/2451 |
| 9,597,186 B2 * | 3/2017 | Nieminen | A61F 2/2442 |
| 9,827,098 B2 | 11/2017 | Mathis et al. |
| 9,827,099 B2 | 11/2017 | Mathis et al. |
| 9,827,100 B2 | 11/2017 | Mathis et al. |
| 9,956,076 B2 | 5/2018 | Mathis et al. |
| 9,956,077 B2 | 5/2018 | Nieminen et al. |
| 10,052,205 B2 | 8/2018 | Mathis et al. |
| 10,166,102 B2 | 1/2019 | Nieminen et al. |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0161393 A1 | 10/2002 | Demond et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0193827 A1 | 12/2002 | McGuckin et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0093148 A1 | 5/2003 | Bolling et al. |
| 2003/0130730 A1 | 7/2003 | Cohn et al. |
| 2003/0135267 A1 | 7/2003 | Solem et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0172046 A1 | 9/2004 | Hlavka et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0260342 A1 | 12/2004 | Vargas et al. |
| 2004/0260384 A1 | 12/2004 | Allen |
| 2005/0004667 A1 | 1/2005 | Swinford et al. |
| 2005/0027351 A1 | 2/2005 | Reuter et al. |
| 2005/0033419 A1 | 2/2005 | Alferness et al. |
| 2005/0060030 A1 | 3/2005 | Lashinski et al. |
| 2005/0085903 A1 | 4/2005 | Lau |

(56) References Cited

U.S. PATENT DOCUMENTS

| | | | |
|---|---|---|---|
| 2005/0096740 A1 | 5/2005 | Langberg et al. | |
| 2005/0107810 A1 | 5/2005 | Morales et al. | |
| 2005/0137449 A1 | 6/2005 | Nieminen et al. | |
| 2005/0137450 A1* | 6/2005 | Aronson | A61F 2/2451 600/37 |
| 2005/0137451 A1* | 6/2005 | Gordon | A61F 2/2451 600/37 |
| 2005/0149182 A1 | 7/2005 | Alferness et al. | |
| 2005/0177228 A1 | 8/2005 | Solem et al. | |
| 2005/0197692 A1 | 9/2005 | Pai et al. | |
| 2005/0197693 A1 | 9/2005 | Pai et al. | |
| 2005/0197694 A1 | 9/2005 | Pai et al. | |
| 2005/0209690 A1 | 9/2005 | Mathis et al. | |
| 2005/0216077 A1 | 9/2005 | Mathis et al. | |
| 2005/0222678 A1 | 10/2005 | Lashinski et al. | |
| 2005/0261704 A1 | 11/2005 | Mathis | |
| 2005/0272969 A1 | 12/2005 | Alferness et al. | |
| 2006/0030882 A1 | 2/2006 | Adams et al. | |
| 2006/0041305 A1 | 2/2006 | Lauterjung | |
| 2006/0116758 A1 | 6/2006 | Swinford et al. | |
| 2006/0142854 A1 | 6/2006 | Alferness et al. | |
| 2006/0161169 A1 | 7/2006 | Nieminen et al. | |
| 2006/0167544 A1 | 7/2006 | Nieminen et al. | |
| 2006/0191121 A1* | 8/2006 | Gordon | A61F 2/2451 29/525.01 |
| 2006/0271174 A1 | 11/2006 | Nieminen et al. | |
| 2007/0066879 A1 | 3/2007 | Mathis et al. | |
| 2007/0239270 A1 | 10/2007 | Mathis et al. | |
| 2008/0015407 A1 | 1/2008 | Mathis et al. | |
| 2008/0015679 A1 | 1/2008 | Mathis et al. | |
| 2008/0015680 A1 | 1/2008 | Mathis et al. | |
| 2008/0071364 A1 | 3/2008 | Kaye et al. | |
| 2010/0280602 A1 | 11/2010 | Mathis | |
| 2011/0066234 A1 | 3/2011 | Gordon et al. | |
| 2011/0106117 A1 | 5/2011 | Mathis et al. | |
| 2012/0123532 A1 | 5/2012 | Mathis | |
| 2012/0197389 A1 | 8/2012 | Alferness et al. | |
| 2016/0310273 A1* | 10/2016 | Nieminen | A61F 2/246 |
| 2016/0374809 A1 | 12/2016 | Mathis et al. | |
| 2016/0374810 A1 | 12/2016 | Mathis et al. | |
| 2017/0079796 A1 | 3/2017 | Nieminen et al. | |
| 2017/0189185 A1 | 7/2017 | Nieminen et al. | |
| 2017/0296341 A1* | 10/2017 | Nieminen | A61F 2/2442 |
| 2018/0243092 A1 | 8/2018 | Mathis et al. | |
| 2018/0256330 A1 | 9/2018 | Wypych | |

FOREIGN PATENT DOCUMENTS

| | | |
|---|---|---|
| EP | 0968688 A1 | 1/2000 |
| EP | 1050274 A1 | 11/2000 |
| EP | 1095634 A2 | 5/2001 |
| EP | 1177779 A2 | 2/2002 |
| EP | 2181670 A2 | 5/2010 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| SE | 9902455 | 12/2000 |
| WO | WO98/56435 A1 | 12/1998 |
| WO | WO00/44313 A1 | 8/2000 |
| WO | WO00/60995 A2 | 10/2000 |
| WO | WO00/74603 A1 | 12/2000 |
| WO | WO01/00111 A1 | 1/2001 |
| WO | WO01/19292 A1 | 3/2001 |
| WO | WO01/50985 A1 | 7/2001 |
| WO | WO01/54618 A1 | 8/2001 |
| WO | WO01/87180 A2 | 11/2001 |
| WO | WO02/00099 A2 | 1/2002 |
| WO | WO02/01999 A2 | 1/2002 |
| WO | WO02/05888 A1 | 1/2002 |
| WO | WO02/19951 A1 | 3/2002 |
| WO | WO02/34118 A2 | 5/2002 |
| WO | WO02/47539 A2 | 6/2002 |
| WO | WO02/053206 A2 | 7/2002 |
| WO | WO02/060352 A1 | 8/2002 |
| WO | WO02/062263 A2 | 8/2002 |
| WO | WO02/062270 A1 | 8/2002 |
| WO | WO02/062408 A2 | 8/2002 |
| WO | WO02/076284 A2 | 10/2002 |
| WO | WO02/078576 A2 | 10/2002 |
| WO | WO02/096275 A2 | 12/2002 |
| WO | WO03/015611 A2 | 2/2003 |
| WO | WO03/037171 A2 | 5/2003 |
| WO | WO03/049647 A1 | 6/2003 |
| WO | WO03/049648 A2 | 6/2003 |
| WO | WO03/055417 A1 | 7/2003 |
| WO | WO03/059198 A2 | 7/2003 |
| WO | WO03/063735 A2 | 8/2003 |
| WO | WO2004/045463 A2 | 6/2004 |
| WO | WO2004/084746 A2 | 10/2004 |
| WO | WO2005/046531 A2 | 5/2005 |
| WO | WO2005/058206 A1 | 6/2005 |
| WO | WO2006/002492 A1 | 1/2006 |

OTHER PUBLICATIONS

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents Induction of Atrial Fibrillation. Circulation. Sep. 16, 1997; 96(6): 1893-1898.

Pelton et al. Medical uses of nitinol; Material Science Forum; vols. 327-328; pp. 63-70; 2000 (held in Kanazawa, Japan, May 1999).

Pijls et al.; Measurement of fractional flow reserve to assess the functional severity of coronary-artery stenoses; The New England J. of Med.; vol. 334; No. 26; pp. 1703-1708; Jun. 27, 1996.

Pai, Suresh; U.S. Appl. No. 60/329,694 entitled "Percutaneous cardiac support structures and deployment means," filed Oct. 16, 2001.

Yamanouchi, et al.; Activation Mapping from the coronary sinus may be limited by anatomic variations; vol. 21 pp. 2522-2526; Nov. 1998.

\* cited by examiner

TISSUE SHAPING DEVICE

CROSS REFERENCE TO RELATED APPLICATIONS

This application is a continuation of U.S. application Ser. No. 15/465,253, filed Mar. 21, 2017, which is a continuation of U.S. application Ser. No. 15/136,739, filed Apr. 22, 2016, now U.S. Pat. No. 9,597,186; which is a continuation of U.S. application Ser. No. 14/642,476, filed Mar. 9, 2015, now U.S. Pat. No. 9,320,600; which is a continuation of U.S. application Ser. No. 12/907,907, filed Oct. 19, 2010, now U.S. Pat. No. 8,974,525; which is a continuation of U.S. application Ser. No. 12/060,781, filed Apr. 1, 2008, now U.S. Pat. No. 7,828,842; which is a continuation of U.S. application Ser. No. 11/275,630, filed Jan. 19, 2006, now U.S. Pat. No. 7,351,260; which is a continuation-in-part of U.S. application Ser. No. 11/132,786, filed May 18, 2005, now abandoned. U.S. application Ser. No. 11/275,630, filed Jan. 19, 2006, also claims the benefit of U.S. Provisional Application No. 60/645,819, filed Jan. 20, 2005. Each of these applications is fully incorporated by reference herein.

BACKGROUND OF THE INVENTION

This invention relates generally to devices and methods for shaping tissue by deploying one or more devices in body lumens adjacent to the tissue. One particular application of the invention relates to a treatment for mitral valve regurgitation through deployment of a tissue shaping device in the patient's coronary sinus or great cardiac vein.

The mitral valve is a portion of the heart that is located between the chambers of the left atrium and the left ventricle. When the left ventricle contracts to pump blood throughout the body, the mitral valve closes to prevent the blood being pumped back into the left atrium. In some patients, whether due to genetic malformation, disease or injury, the mitral valve fails to close properly causing a condition known as regurgitation, whereby blood is pumped into the atrium upon each contraction of the heart muscle. Regurgitation is a serious, often rapidly deteriorating, condition that reduces circulatory efficiency and must be corrected.

Two of the more common techniques for restoring the function of a damaged mitral valve are to surgically replace the valve with a mechanical valve or to suture a flexible ring around the valve to support it. Each of these procedures is highly invasive because access to the heart is obtained through an opening in the patient's chest. Patients with mitral valve regurgitation are often relatively frail thereby increasing the risks associated with such an operation.

One less invasive approach for aiding the closure of the mitral valve involves the placement of a tissue shaping device in the cardiac sinus, a vessel that passes adjacent the mitral valve annulus. (As used herein, "coronary sinus" refers to not only the coronary sinus itself, but also to the venous system associated with the coronary sinus, including the great cardiac vein.) The tissue shaping device is designed to reshape the vessel and surrounding valve tissue to reshape the valve annulus and other components, thereby promoting valve leaflet coaptation. This technique has the advantage over other methods of mitral valve repair because it can be performed percutaneously without opening the chest wall. Examples of such devices are shown in U.S. application Ser. No. 10/142,637, "Body Lumen Device Anchor, Device and Assembly" filed May 8, 2002, now U.S. Pat. No. 6,824,562; U.S. application Ser. No. 10/331,143, "System and Method to Effect the Mitral Valve Annulus of a Heart" filed Dec. 26, 2002, now U.S. Pat. No. 6,793,673; U.S. application Ser. No. 10/429,172, "Device and Method for Modifying the Shape of a Body Organ," filed May 2, 2003; and U.S. application Ser. No. 10/742,600 filed Dec. 19, 2003.

SUMMARY OF THE INVENTION

Tissue shaping devices can encounter material stress while in storage, during deployment and after implant. Repeated stress can lead to material fatigue and breakage. The present invention provides a tissue shaping device with improved stress response characteristics.

One aspect of the invention provides a tissue shaping device adapted to be disposed in a vessel near a patient's heart to reshape the patient's heart. The tissue shaping device has an expandable proximal anchor; a proximal anchor lock adapted to lock the proximal anchor in an expanded configuration; an expandable distal anchor; a distal anchor lock adapted to lock the distal anchor in an expanded configuration; and a connector disposed between the proximal anchor and the distal anchor, with the connector having a substantially non-circular cross-section, such as a substantially rectangular or substantially oval cross-section.

In some embodiments, the distal anchor lock includes a bend in the connector and, optionally, a compliant element adjacent the bend in the connector, with at least the compliant element being adapted to change shape during a distal anchor locking operation. In some embodiments the distal anchor lock has an anchor lock element adapted to move with respect to the connector as the distal anchor expands.

In some embodiments, the connector is a first connector, and the device also has a second connector extending between the proximal and distal anchors. The distal anchor lock may make up at least part of the wire element. The second connector can be adapted to provide fatigue resistance.

In some embodiments, the distal anchor has a crimp and a wire element extending from the crimp, the wire element having a strain relief portion extending distal of the crimp to form a bend extending substantially below a plane defined by the crimp. The distal anchor wire element may also have a vessel engagement portion extending proximally from the strain relief portion and away from the crimp and a lock portion extending from the vessel engagement portion to form part of the distal lock.

In further embodiments, the proximal anchor can include a crimp and a wire element extending from the crimp, with the wire element having a strain relief portion extending distal of the crimp to form a bend extending substantially below a plane defined by the crimp. The proximal anchor wire element further may also have a vessel engagement portion extending proximally from the strain relief portion and away from the crimp and a lock portion extending from the vessel engagement portion and forming part of the proximal lock.

Another aspect of the invention provides a tissue shaping device adapted to be disposed in a vessel near a patient's heart to reshape the patient's heart. The tissue shaping device may include an expandable proximal anchor, with the proximal anchor having a crimp and a wire element extending from the crimp and the wire element having a strain relief portion extending distal of the crimp to form a bend extending substantially below a plane defined by the crimp. The tissue shaping device may also have an expandable distal anchor, with the distal anchor comprising a crimp and a wire element extending from the crimp and the wire element having a strain relief portion extending distal of the crimp to form a bend extending substantially below a plane defined by the crimp. The tissue shaping device may also have a connector extending between the proximal anchor crimp and the distal anchor connector crimp.

In some embodiments, the proximal anchor wire element further includes a vessel engagement portion extending proximally from the strain relief portion and away from the crimp, a vessel engagement portion extending proximally from the strain relief portion and away from the crimp, a proximal anchor lock adapted to lock the proximal anchor in an expanded configuration, and/or a distal anchor lock adapted to lock the distal anchor in an expanded configuration.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
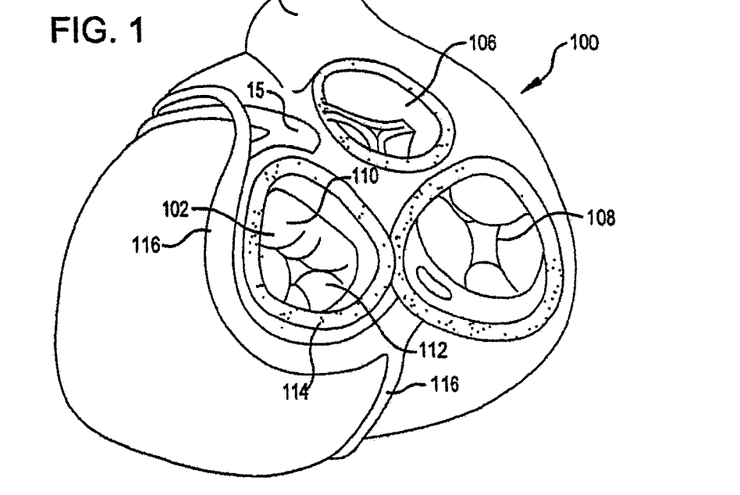
FIG. 1 is a schematic view of a human heart with the atria removed.

FIG. 1 is a superior view of a heart 100 with the atria removed. As pictured, the heart comprises several valves including mitral valve 102, pulmonary valve 104, aortic valve 106 and tricuspid valve 108. Mitral valve 102 includes anterior cusp 110, posterior cusp 112 and annulus 114. Annulus 114 encircles cusps 110 and 112 and functions to maintain their respective spacing to ensure complete mitral valve closure during left ventricular contractions of the heart 100. As illustrated, coronary sinus 116 partially encircles mitral valve 102 and is adjacent to mitral valve annulus 114. Coronary sinus 116 is part of the venous system of heart 100 and extends along the AV groove between the left atrium and the left ventricle. This places coronary sinus 116 essentially within the same plane as mitral valve annulus 114, making coronary sinus 116 available for placement of shaping device 200 in order to effect mitral valve geometry and to restore proper valve function.

Figure 2:
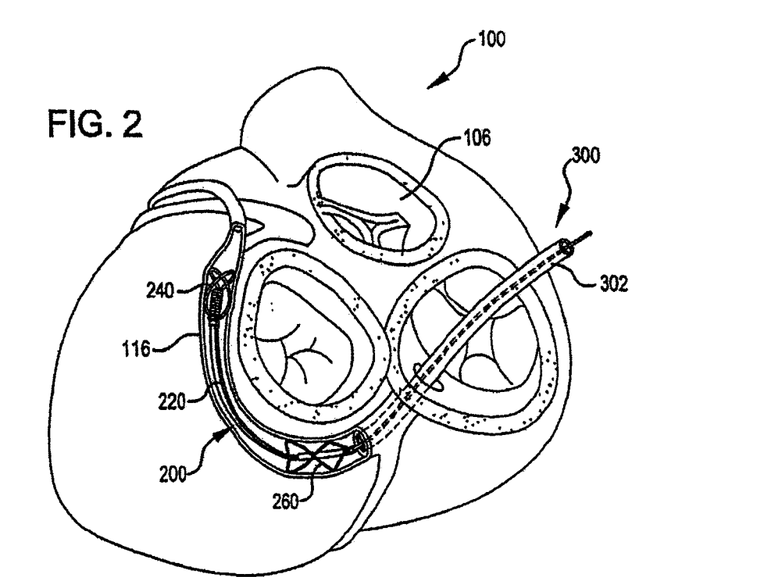
FIG. 2 is a schematic view of a human heart showing the deployment of a tissue shaping device in the coronary sinus.

FIG. 2 illustrates one possible embodiment of an implantable shaping device 200, which is deployable in coronary sinus 116 or other body lumen. As illustrated in FIG. 2, device 200 generally comprises an elongated connector 220 disposed between a distal anchor 240 and a proximal anchor 260. Both distal anchor 240 and proximal anchor 260 are shown in their deployed (i.e. expanded) configuration in FIG. 2, securely positioned within the coronary sinus 116. FIG. 2 further depicts, in phantom, a deployment system 300 comprising catheter 302 for delivering and positioning shaping device 200 in the coronary sinus 116. Further details of the delivery system may be found in U.S. application Ser. Nos. 10/946,332 and 10/945,855.

Figure 3:
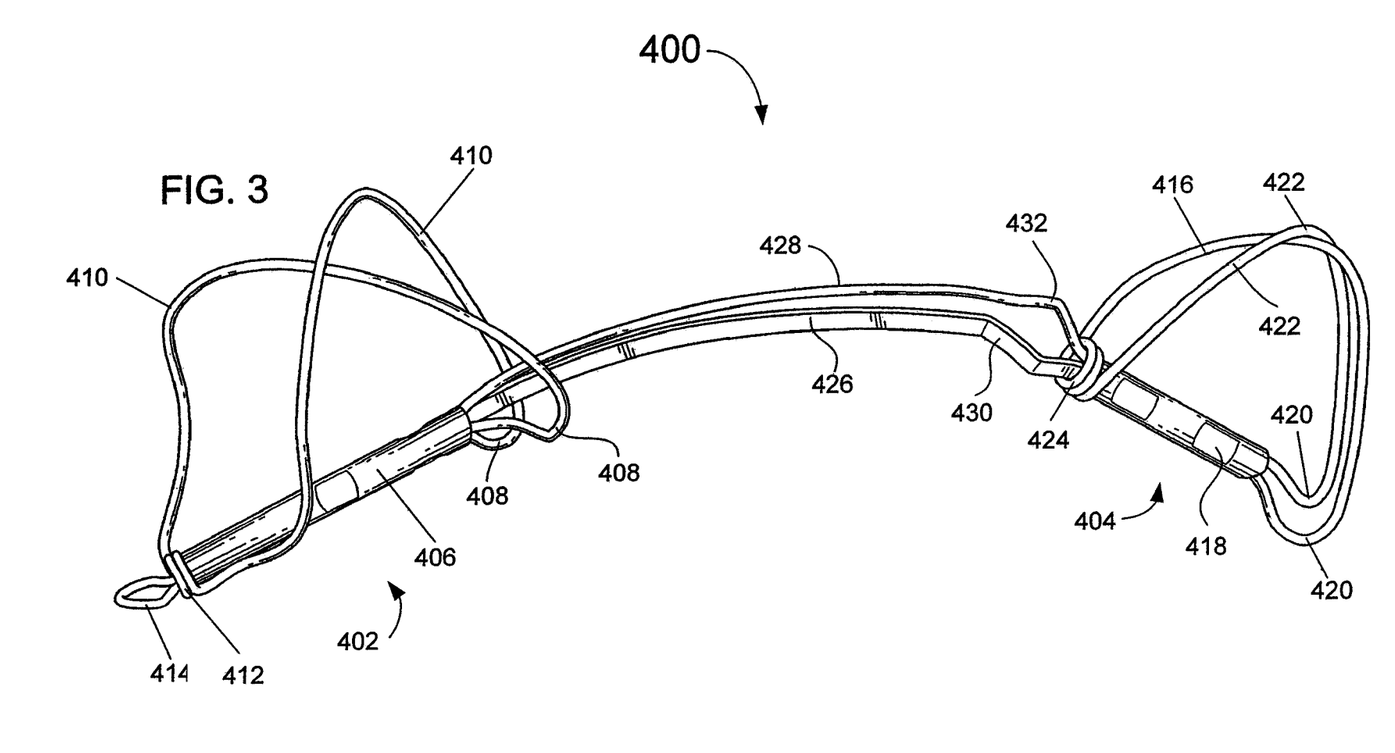
FIG. 3 is a perspective view of a tissue shaping device according to one embodiment of this invention.
Figure 4:
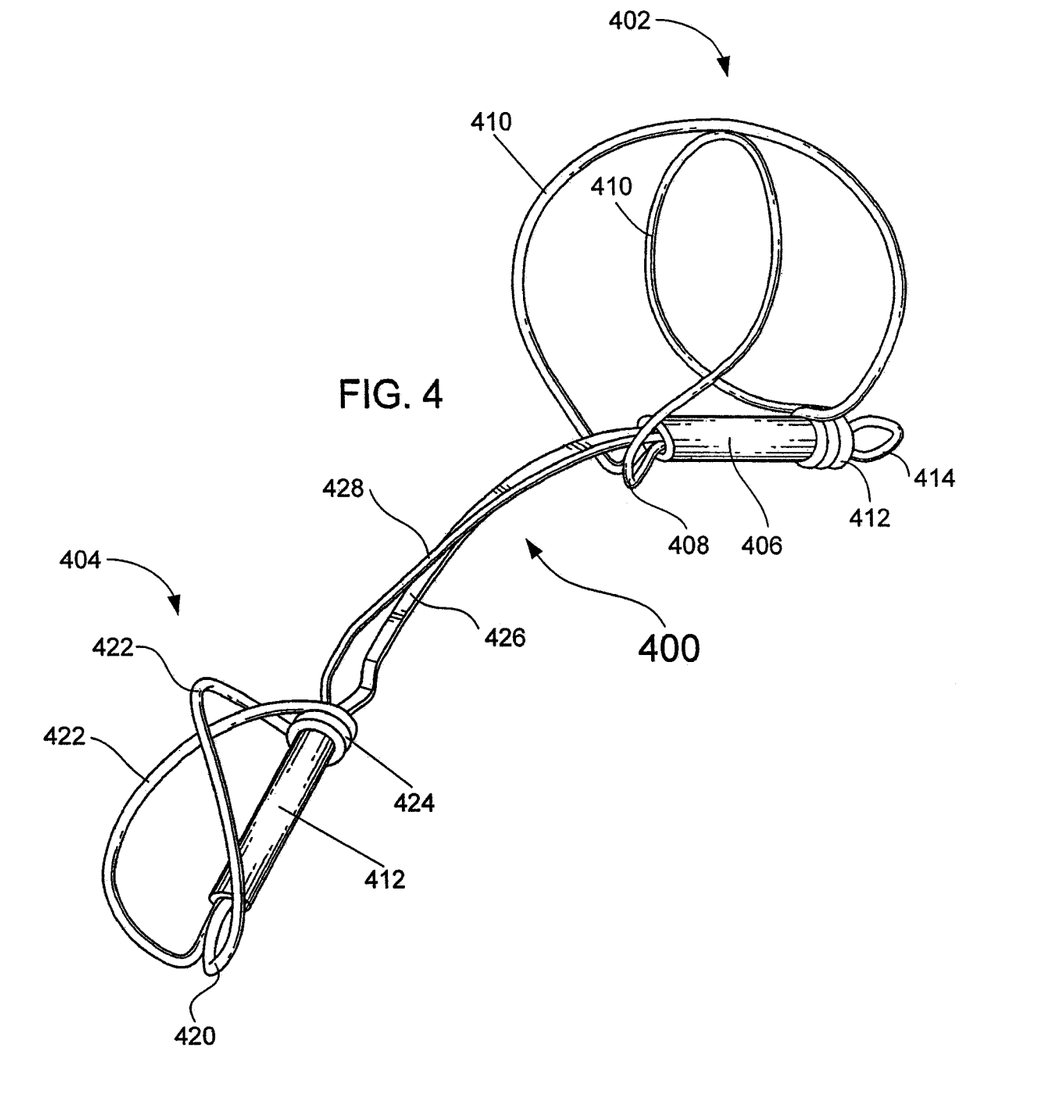
FIG. 4 is another perspective view of the tissue shaping device of FIG. 3.
Figure 5:
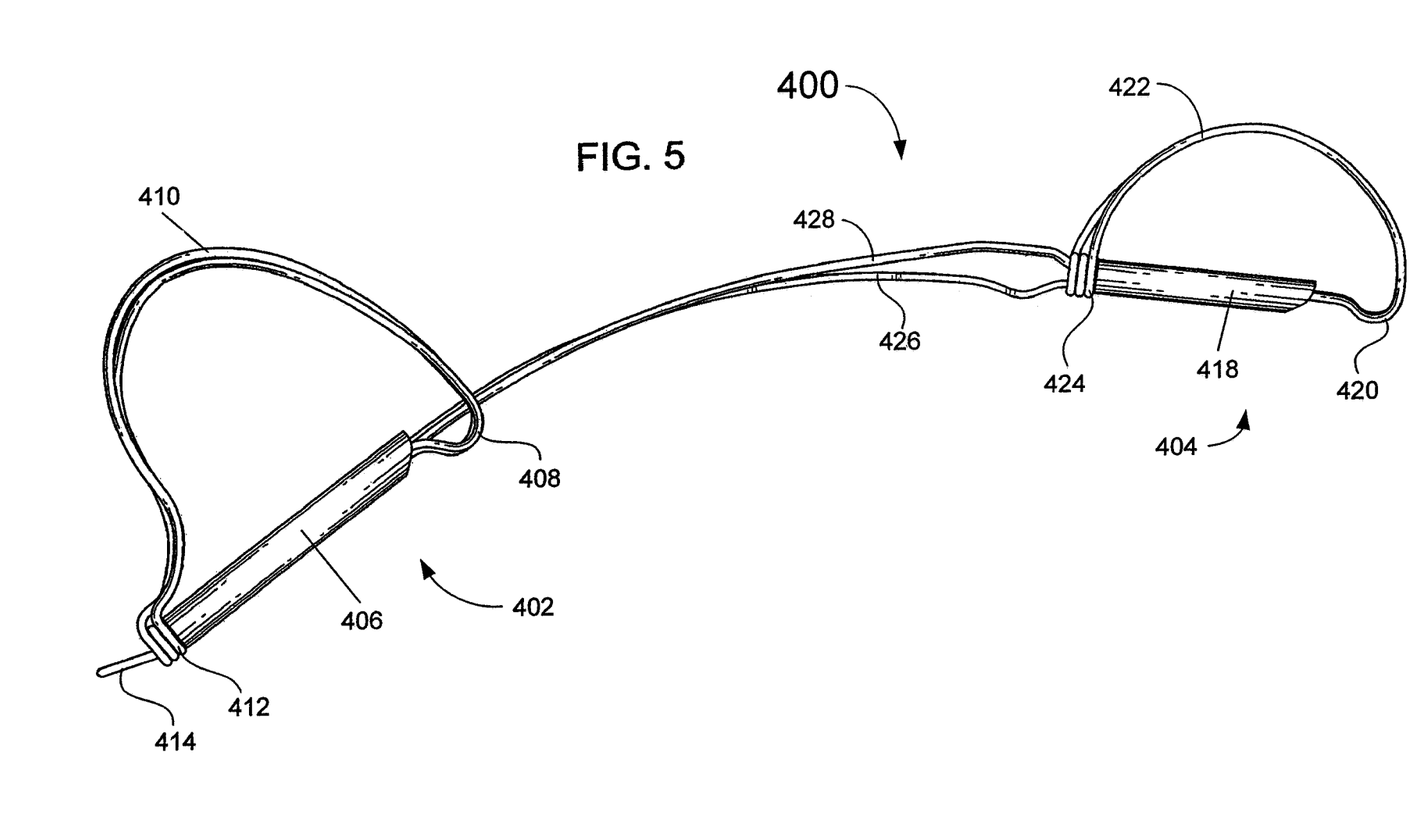
FIG. 5 is side elevational view of the tissue shaping device of FIGS. 3 and 4.

FIGS. 3-5 show one embodiment of a tissue shaping device 400 with proximal anchor 402 and distal anchor 404 in their expanded and locked configurations. In this embodiment, proximal anchor 402 is made from a shape memory metal wire (such as Nitinol) extending from a crimp 406. Stress relief portions 408 of the wire extend distal to crimp 406; the purpose of these stress relief features will be discussed below with reference to FIG. 6. The wire extends upward from stress relief portions 408 to form vessel engagement portions 410 which cross to form a FIG. 8 pattern, as shown. Vessel engagement portions 410 and crimp 406 engage the inner wall of the coronary sinus or other vessel in which the device is implanted. The wire also forms a lock loop 412 which interacts with an arrowhead-shaped element 414 extending from the proximal end of the crimp to form the proximal anchor lock. Actuation of the proximal anchor lock is described in U.S. application Ser. No. 10/946,332, now U.S. Pat. No. 7,837,729, and Ser. No. 10/945,855, now U.S. Pat. No. 8,182,529.

Likewise, distal anchor is made from a shape memory wire 416 extending from a crimp 418. Stress relief portions 420 of the wire extend distal to crimp 418. Wire 416 extends upward from stress relief portions 420 to form vessel engagement portions 422 which cross to form a FIG. 8 pattern, as shown. Vessel engagement portions 422 and crimp 418 engage the inner wall of the coronary sinus or other vessel in which the device is implanted. Wire 416 also forms a lock loop 424.

Extending between anchors 402 and 404 are a substantially flat connector 426 and a wire connector 428. In this embodiment, connectors 426 and 428 are both made of shape memory metal, such as Nitinol. When device 400 is deployed within the coronary sinus or other vessel, the distal anchor 404 is deployed from the delivery catheter first, then expanded and locked to maintain its position within the vessel. A proximal cinching force is then applied on the distal anchor from, e.g., a tether attached to arrowhead element 414 until an appropriate amount of reshaping of the mitral valve or other tissue has occurred (as determined, e.g., by viewing blood flow with fluoroscopy, ultrasound, etc.). While maintaining the cinching force, proximal anchor 402 is deployed from the delivery catheter, expanded and locked in the expanded configuration. The device 400 may then be released from the delivery system's tether. By spanning the distance between proximal anchor 402 and distal anchor 404, connectors 426 and 428 maintain the reshaping force on the tissue.

When deployed in the coronary sinus to reshape the mitral valve annulus, the tissue shaping devices of this invention are subjected to cyclic bending and tensile loading as the patient's heart beats. Device 400 differs from prior tissue shaping devices by changing the cross-sectional profile of the connector, in this illustration by making connector 426 substantially flat. This shape provides improved fatigue resistance over prior devices whose wire connectors had a round profile. In addition, the flat shape of connector 426 helps device 400 to orient itself within the vessel during the deployment process. In alternative embodiments, connector 426 may have a more round shape, with, e.g., an oval cross-section or other non-circular cross-section instead of a rectangular cross-section.

Prior to use, tissue shaping devices such as those shown in FIGS. 3-5 may be stored in cartridges or other containers, such as described in U.S. application Ser. Nos. 10/946,332 and 10/945,855, then delivered to the coronary sinus or other vessel in a delivery catheter, as shown in FIG. 2. During storage and delivery, the device may be compressed in the directions shown by the arrows in FIG. 6 from an unstressed expanded shape into an unexpanded configuration, such as the configuration shown in phantom in FIG. 6. There are two aspects of stresses experienced by the device. In one aspect stress may be imparted while the device is collapsed for storage and delivery. While collapsed it is possible that the change of shape from unstressed configuration to collapsed condition creates an area of higher stress. Anchor wire forms are designed with stress reliving element (420) to reduce this type of stress on implant while in storage or during deployment. Another aspect of stress on implant happens when it is deployed, locked, and detached from the delivery catheter. This type of stress comes from the repeated motion (fatigue) of heart increasing bending stress on implant. This could result in implant fracture. The connector element design (426) with flat ribbon provides resistance to this bending stress thus reducing chances of fatigue fracture. In this embodiment, therefore, the device is provided with stress relief features. Bent portions 408 of the proximal anchor wire provide extra stress relief while the device is in storage and relieves material stress on the wire that would otherwise be present where the wire emerges from crimp 406. Similar stress relief bends 420 in distal anchor wire 416 serve a similar function.

Figure 6:
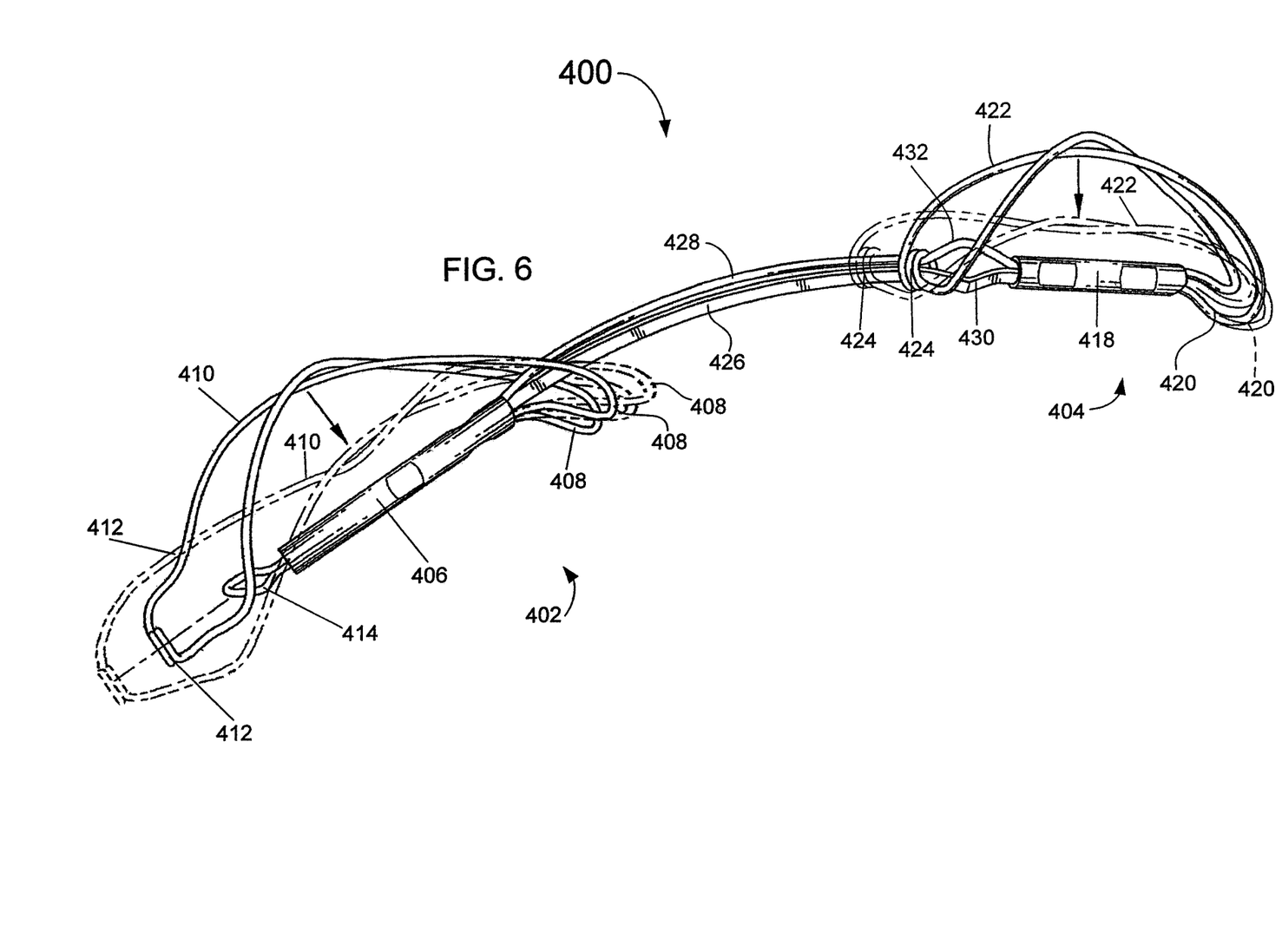
FIG. 6 is a perspective view showing the device of FIG. 3 in an unexpanded configuration and in a partially expanded configuration.

FIG. 6 shows device 400 in a compressed storage configuration (shown in phantom) and in a partially expanded but not yet locked configuration. After emerging from the delivery catheter, the shape memory characteristics of anchors 402 and 404 will cause them to expand to, e.g., the configuration shown in solid line in FIG. 6. After the user confirms that the device is in the desired position, the user may then employ the device delivery system (such as that described in U.S. application Ser. Nos. 10/946,332 and 10/945,855) to lock the distal anchor by moving lock loop 424 distally with respect to the connector. Distal movement of lock loop 424 beyond the position shown in FIG. 6 will cause bent portions 430 and 432 of connectors 426 and 428, respectively, to move toward each other, permitting lock loop to pass over them to the position shown in FIG. 1, thereby locking the distal anchor in an expanded configuration. After placement of the proximal anchor in its desired position (after, e.g., application of a proximally directed cinching force), proximal anchor lock loop 412 may be advanced distally over arrowhead element 414 to lock the proximal anchor in an expanded configuration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of modifying the geometry of a mitral valve, comprising:
   delivering a tissue shaping device to a coronary sinus;
   deploying a distal anchor from a delivery device and into the coronary sinus to allow the expandable distal anchor to expand;
   applying a proximal cinching force to the distal anchor to reshape tissue;
   while maintaining the proximal cinching force, deploying the proximal anchor from the delivery device to allow the proximal anchor to expand; and
   locking the proximal anchor in a locked configuration after allowing the proximal anchor to expand.

2. The method of claim 1, further comprising locking the distal anchor in a locked configuration after allowing the distal anchor to self-expand.

3. The method of claim 1, wherein locking the proximal anchor occurs while maintaining the proximal cinching force.

* * * * *